United States Patent
Higuchi et al.

(10) Patent No.: US 8,932,865 B2
(45) Date of Patent: *Jan. 13, 2015

(54) METHOD FOR QUANTIFYING THE AMOUNT OF CHOLESTEROL IN HIGH-DENSITY LIPOPROTEIN 3

(75) Inventors: Maiko Higuchi, Gosen (JP); Yasuki Itoh, Gosen (JP)

(73) Assignee: Denka Seiken Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/809,223

(22) PCT Filed: Jul. 22, 2011

(86) PCT No.: PCT/JP2011/066674
§ 371 (c)(1),
(2), (4) Date: Feb. 28, 2013

(87) PCT Pub. No.: WO2012/011556
PCT Pub. Date: Jan. 26, 2012

(65) Prior Publication Data
US 2013/0157374 A1 Jun. 20, 2013

(30) Foreign Application Priority Data
Jul. 23, 2010 (JP) .................... 2010-166376

(51) Int. Cl.
*G01N 33/92* (2006.01)
*G01N 33/48* (2006.01)
*C12Q 1/60* (2006.01)
*C12Q 1/44* (2006.01)

(52) U.S. Cl.
CPC ........ *G01N 33/92* (2013.01); *C12Q 1/60* (2013.01); *G01N 2405/00* (2013.01); *C12Q 1/44* (2013.01)
USPC ................... 436/71; 436/63; 435/11

(58) Field of Classification Search
USPC ................... 436/63, 71; 435/11, 29
See application file for complete search history.

(56) References Cited

U.S. PATENT DOCUMENTS

| 6,194,164 B1 | 2/2001 | Matsui et al. | |
| 2009/0181413 A1* | 7/2009 | Itoh et al. | 435/11 |
| 2012/0208219 A1* | 8/2012 | Itoh et al. | 435/11 |

FOREIGN PATENT DOCUMENTS

| EP | 1046716 A1 | 10/2000 |
| EP | 1 930 443 A1 | 6/2008 |
| JP | 9-299 A | 1/1997 |
| JP | 2001-346598 A | 12/2001 |
| JP | 2009-207463 A | 9/2009 |
| WO | WO 98/47005 A1 | 10/1998 |
| WO | WO 99/10526 A1 | 3/1999 |
| WO | WO 2005/100591 A1 | 10/2005 |

OTHER PUBLICATIONS

Okada et al. Journal of Clinical Laboratory Analysis, vol. 15, 2001, pp. 223-229.*
International Search Report issued in PCT/JP2011/066674, mailed on Oct. 18, 2011.
Ahmadraji, T. et al, "The evolution of selective analysis of HDL and LDL cholesterol in clinical and point of care testing," Analytical Methods, Aug. 7, 2013, vol. 5, pp. 3612-3625.
Extended European Search Report for Appl. No. 118097260 dated Dec. 17, 2013.
Ito, Y. et al, "Development of a homogeneous assay for measurement of high-density lipoprotein-subclass cholesterol," Clinica Chimica Acta, Sep. 19, 2013, vol. 427, pp. 86-93.
Okada, M. et al, "Direct Measurement of HDL Cholesterol: Method of Eliminating Apolipoprotein E-Rich Particles," Journal of Clinical Laboratory Analysis, Jan. 1, 2001, vol. 15, pp. 223-229.

* cited by examiner

*Primary Examiner* — Maureen Wallenhorst
(74) *Attorney, Agent, or Firm* — Birch, Stewart, Kolasch & Birch, LLP (57) ABSTRACT

A method that enables quantification of cholesterol in high-density lipoprotein 3 (HDL3) in a test sample without requiring a laborious operation is disclosed. The method for quantifying cholesterol in HDL3 having: Step 1 wherein a surfactant that reacts with lipoproteins other than high-density lipoprotein 3 is reacted with a test sample to transfer cholesterol to the outside of the reaction system; and Step 2 in which cholesterol remaining in the reaction system is quantified. The method enables specific quantification of HDL3 cholesterol in a test sample using an automatic analyzer without requirement of a laborious operation such as ultracentrifugation or pretreatment. Further, quantification of the HDL2 cholesterol level can also be carried out by subtracting the HDL3 cholesterol level from the total HDL cholesterol level obtained by a conventional method for quantifying the total HDL cholesterol in a test sample.

13 Claims, 3 Drawing Sheets

METHOD FOR QUANTIFYING THE AMOUNT OF CHOLESTEROL IN HIGH-DENSITY LIPOPROTEIN 3

TECHNICAL FIELD

The present invention relates to a method for quantifying cholesterol in high-density lipoprotein 3 (which may be hereinafter referred to as "HDL3") (cholesterol in HDL3 may be hereinafter referred to as "HDL3 cholesterol").

BACKGROUND ART

Since high-density lipoprotein (HDL) receives cholesterol from various tissues including walls of blood vessels with arteriosclerosis, it is involved in the action of removal of cholesterol accumulated in cells. Therefore, HDL cholesterol is also called the reverse cholesterol transport system. High-density lipoprotein is known to have a negative correlation with arteriosclerotic diseases such as coronary arteriosclerosis. Accordingly, an HDL value lower than a predetermined lower limit is regarded as an indication of dislipidemia, and the value is known to be useful as an index of arteriosclerosis.

HDL is constituted by apoprotein, phospholipid, cholesterol and triglyceride. HDL has a density of d=1.063 to 1.210 g/mL, and can be divided into two fractions, that is, HDL2 wherein d=1.063 to 1.125 g/mL and HDL3 wherein d=1.125 to 1.210 g/mL. A notch is found at the portion of d=1.125 in the distribution curve of lipoprotein, and the part having higher densities in the curve corresponds to HDL3. Alternatively, HDL can be divided into subfractions based on the difference in the content of apolipoprotein E among apoproteins in HDL, and HDLs having higher contents of apoE are defined as apoE-rich HDL.

In terms of the functions, HDL has been conventionally studied as a whole, but each of the subfractions HDL2 and HDL3 is now known to have unique functions. It is clinically known that CETP deficiency prevents cholesterol transport from HDL to LDL and IDL, leading to an increase in the HDL cholesterol level. The HDL increased by CETP deficiency is HDL2. HDL2 is said to have an antiarteriosclerotic action. It is also said that CETP deficiency causes an increase in apoE-rich HDL, and that, since apoE-rich HDL has a strong cholesterol-drawing ability and antiplatelet action, it is a good HDL. Further, a decrease in the hepatic lipase activity prevents conversion of HDL3 to HDL2, resulting in an increase in HDL3. It is suggested that increased HDL3 leads to increased incidence rates of coronary artery diseases. In view of such tendencies, it is expected that measurement of each HDL subfraction may contribute to judgment of whether or not a patient is suffering from an arteriosclerotic disease and of the cause of the disease. Further, at present, in view of these functions of HDL subfractions, manufacturers are developing therapeutic agents that inhibit the function of CETP, decrease the LDL cholesterol level, and increase the HDL cholesterol level.

Establishment of a simple method for measuring the HDL subfractions may lead to detailed elucidation of their functions, and to their therapeutic effects in the future.

Examples of methods for measuring HDL subfractions which have been known so far include ultracentrifugation, high-performance liquid chromatography (HPLC), HDL3 precipitation (Patent Document 1) and NMR.

In ultracentrifugation, fractionation is carried out utilizing the difference in the density of lipoprotein. This method has drawbacks in that the operation requires a skill; the method takes many days; and the cost is high. In the method by Okazaki et al. wherein HPLC is used for separating HDL2 and HDL3, the operation takes a long time, and special equipment is required. HDL3 precipitation is a method wherein a reagent containing a divalent metal ion and dextran sulfate is used to aggregate lipoproteins other than HDL3, and HDL3 in the supernatant portion is recovered by centrifugation and measured using an automatic analyzer. This method is not widely used since the method has drawbacks in that the operation of this method also requires a skill; the method is a manual method; the method requires an operation of sample pretreatment; and a certain length of time is required before measurement. Further, NMR, which is a method wherein the number of particles of lipoprotein is measured by magnetic resonance, is not commonly employed since the method requires special equipment.

There is another method for analyzing an HDL subfraction (Patent Document 2). Although this method enables measurement with a general purpose automatic analyzer, the method employs a method wherein a surfactant is used to prevent an enzyme from acting on lipoproteins other than HDL3. Therefore, since the HDL3 reaction is allowed to proceed in the presence of the lipoproteins other than the lipoprotein of interest, the measurement might be influenced by such lipoproteins or, in cases where the prevention is not sufficient, the lipoproteins other than HDL3 might be undesirably measured together.

Thus, as an alternative to the above methods, a reagent which enables simple and more selective quantification of the cholesterol level needs to be invented.

PRIOR ART DOCUMENTS

Patent Documents

[Patent Document 1] JP 2009-207463 A
[Patent Document 2] JP 2001-346598 A

SUMMARY OF THE INVENTION

Problems to be Solved by the Invention

An object of the present invention is to provide a method that enables quantification of HDL3 in a test sample without requiring a laborious operation.

Means for Solving the Problems

The present inventors intensively studied to discover surfactants that react with lipoproteins other than high-density lipoprotein 3 but hardly react with high-density lipoprotein 3. The present inventors then inferred that HDL3 cholesterol in a test sample can be quantified by reacting such a surfactant with the test sample and subsequently quantifying cholesterol in the remaining HDL3. The present inventors experimentally confirmed that this is possible, thereby completing the present invention.

That is, the present invention provides a method for quantifying cholesterol in high-density lipoprotein 3, said method comprising:

Step 1 wherein a surfactant(s) that react(s) with lipoproteins other than high-density lipoprotein 3 is/are reacted with a test sample to transfer cholesterol to the outside of the reaction system; and Step 2 wherein cholesterol remaining in the reaction system is quantified.

Effect of the Invention

By the present invention, HDL3 cholesterol in a test sample can be specifically quantified with an automatic analyzer without requirement of a laborious operation such as ultracentrifugation or pretreatment. Further, quantification of the HDL2 cholesterol level can also be carried out by subtracting the HDL3 cholesterol level from the total HDL cholesterol level obtained by a conventional method for quantifying the total HDL cholesterol in a test sample.

BEST MODE FOR CARRYING OUT THE INVENTION

The test sample to be subjected to the method of the present invention is not restricted as long as HDL3 cholesterol in the sample can be quantified, and the test sample is preferably serum or blood plasma, or a dilution thereof. Serum or a dilution thereof is especially preferred.

In Step 1 of the present invention, a surfactant that reacts with lipoproteins other than HDL3 is reacted with a test sample. Examples of the surfactant that reacts with lipoproteins other than HDL3 include, but are not limited to, non-ionic surfactants such as polyoxyethylene distyrene-modified phenyl ether, polyoxyethylene-polyoxypropylene condensates and polyoxyethylene-stearylamine; anionic surfactants such as amide ether sulfate; amphoteric surfactants such as coconut oil fatty acid-amidopropyldimethyl-aminoacetic acid betaine, alkyl dimethyl-aminoacetic acid betaine and lauryl betaine; and cationic surfactants such as lauryl trimethyl ammonium chloride. More specifically, examples of the nonionic surfactants include polyoxyethylene distyrene-modified phenyl ether Emulgen A500 (trade name; manufactured by Kao Corporation; company names hereinafter represent names of manufacturers, and all names described together with company names hereinafter represent trade names), polyoxyethylene-polyoxypropylene condensates Pluronic F127 (ADEKA Corporation), Pluronic F68 (ADEKA Corporation) and Pluronic P103 (ADEKA Corporation) and polyoxyethylene-stearylamine Nymeen S210 (NOF Corporation); examples of the anionic surfactants include amide ether sulfate Sunamide CF-10 (NOF Corporation); examples of the amphoteric surfactants include a coconut oil fatty acid-amidopropyldimethyl-aminoacetic acid betaine Nissan Anon BDF-SF (NOF Corporation), alkyl dimethyl-aminoacetic acid betaine Nissan Anon BF (NOF Corporation) and lauryl betaine Amphitol 24B (Kao Corporation); and the cationic surfactants include lauryl trimethyl ammonium chloride Kohtamin 24P (Kao Corporation). Each of these may be used alone, or two or more types of these may be used in combination.

The concentration of the surfactant that reacts with lipoproteins other than HDL3 is preferably 0.01 to 5.0% by weight, more preferably about 0.03 to about 3.0% by weight.

When the term "react" is used for a surfactant in the present invention, the term means that the surfactant leads lipoprotein to the outside of the reaction system, making an enzyme act easily, or means to protect lipoprotein such that an enzyme cannot act on the lipoprotein.

When the surfactant is reacted with a test sample, HDL3 is hardly affected, so that HDL3 can be quantified in the subsequent step.

The present inventors further discovered that phospholipase and sphingomyelinase act on lipoprotein but hardly act on HDL3. Therefore, by allowing phospholipase and/or sphingomyelinase to coexist with the surfactant, HDL3 cholesterol can be more accurately quantified, which is preferred.

The phospholipase is not restricted as long as it acts on phosphatidyl choline. Phospholipase A, phospholipase C and phospholipase D are preferred, and phospholipase C and phospholipase D are especially preferred. Since the phospholipase and the like are commercially available, commercially available products may be preferably used. Each of the phospholipase and/or the like may be used alone, or two or more types of the phospholipase and/or the like may be used in combination.

The final concentration of the phospholipase and/or the like (total concentration, in cases where two or more types of the phospholipase and/or the like are used—the same applies hereinafter) is preferably about 0.1 to about 100 U/mL, more preferably about 0.2 to about 50 U/mL.

Also in cases where Step 1 is carried out in the coexistence of a surfactant, the reaction conditions (reaction temperature, time, buffer and the like) are as described above.

In Step 1 of the method of the present invention, cholesterol is transferred to the outside of the reaction system by the action(s) of the phospholipase and/or the like. The term "transferred to the outside of the reaction system" herein means that cholesterol and esters thereof are eliminated or protected such that the cholesterol and esters thereof are not involved in the later steps.

The term "elimination" herein means that cholesterol of lipoprotein in a test sample is degraded such that the cholesterol does not affect the reaction for measurement of cholesterol in a later step. Examples of the method for eliminating lipoprotein cholesterol include a method wherein cholesterol esterase and cholesterol oxidase are allowed to act on the cholesterol, followed by decomposition of the produced hydrogen peroxide into water and oxygen using catalase. Alternatively, a hydrogen donor may be reacted with the produced hydrogen peroxide using peroxidase to convert the hydrogen peroxide to a colorless quinone. The method for eliminating lipoprotein cholesterol is not restricted to these. The method of elimination of cholesterol per se is known in the art, and is also described concretely in Examples below.

The term "protection" means to protect lipoprotein in a test sample such that the lipoprotein does not react upon cholesterol measurement in a later step. Examples of the method of protection of lipoprotein include, but are not limited to, a method wherein a surfactant is used to specifically protect each lipoprotein such that cholesterol esterase and cholesterol oxidase do not act on the lipoprotein.

In Step 1, it is possible to sequentially carry out the step of reacting the surfactant and the step of transferring the exposed cholesterol to the outside of the reaction system, but it is also possible to simultaneously carry out these steps as a single step by preliminarily adding the surfactant as well as an enzyme system and a surfactant for transferring the exposed cholesterol to the outside of the reaction system. The latter is preferred because of its simplicity.

In Step 1, in cases where cholesterol esterase and cholesterol oxidase are used, the concentration (the concentration means the final concentration unless otherwise specified in the present specification) of cholesterol esterase is preferably about 0.1 to about 10.0 U/mL, more preferably about 0.2 to about 2.0 U/mL. The concentration of cholesterol oxidase is preferably about 0.05 to about 10.0 U/mL, more preferably about 0.1 to about 1.0 U/mL. The cholesterol esterase is not restricted as long as it acts on ester-type cholesterol, and examples of the cholesterol esterase which may be used include commercially available products such as cholesterol esterase (CEBP, CEN) manufactured by Asahi Kasei Corporation and cholesterol esterase (COE-311, COE-312) manufactured by Toyobo Co., Ltd. Further, the cholesterol oxidase is not restricted as long as it acts on free cholesterol, and examples of the cholesterol oxidase which may be used include commercially available products such as cholesterol oxidase (CONII) manufactured by Asahi Kasei Corporation and cholesterol oxidase (COO-311, COO-321, COO-331) manufactured by Toyobo Co., Ltd.

In Step 1, in cases where peroxidase is used, the concentration of peroxidase is preferably about 2.0 to about 5.0 U/mL, more preferably about 3.0 to about 4.0 U/mL. In cases where a compound for conversion into a colorless quinone is used, the concentration of the compound is preferably about 0.4 to about 0.8 mmol/L.

As the reaction liquid to be used in Step 1, various buffers used in normal biochemical reactions may be used, and the pH of the reaction liquid is preferably between 5 and 8. The solution is preferably Good's, Tris, phosphate or glycine buffer solution, and is preferably a Good's buffer such as bis(2-hydroxyethyl)iminotris(hydroxyethyl)methane(Bis-Tris), piperazine-1,4-bis(2-ethanesulfonic acid) (PIPES), piperazine-1,4-bis(2-ethanesulfonic acid) sesqui sodium salt monohydrate (PIPES 1.5Na), 3-morpholinopropanesulfonic acid (MOPSO), N,N-bis(2-hydroxyethyl)-2-aminoethanesulfonic acid (BES), 2-[4-(2-hydroxyethyl)-1-piperazinyl] ethanesulfonic acid (HEPES) or piperazine-1,4-bis(2-hydroxy-3-propanesulfonic acid) (POPSO).

The reaction temperature in Step 1 is preferably about 25 to about 40° C., more preferably 35 to 38° C., most preferably 37° C. The reaction time is not restricted, and is usually about 2 to about 10 minutes.

Thereafter, in Step 2, cholesterol remaining in the reaction system is quantified. This can be carried out by allowing reaction with a surfactant that reacts with at least HDL3, to quantify the exposed cholesterol. The "surfactant that reacts with at least HDL3" includes a surfactant that specifically reacts with HDL3, surfactant that specifically reacts with HDL (that is, reacts with HDL2 and HDL3) and surfactant that reacts with all lipoproteins.

Examples of the surfactant which may be used in Step 2 include nonionic surfactants such as polyoxyethylene distyrene-modified phenyl ether, polyoxyethylene lauryl ether and p-isooctyl polyoxyethylene phenol formaldehyde polymers; amphoteric surfactants such as lauryl dimethyl-aminoacetic acid betaine; cationic surfactants such as fatty acid series phosphoric acid ester; nonionic surfactants having an HLB of 11 to 14 such as polyoxyethylene distyrene-modified phenyl ether, polyoxyethylene tribenzyl phenyl ether, polyoxyalkylene alkyl ether, polyoxyethylene polycyclic phenyl ether and polyoxyethylene cumyl phenyl ether; imidazoline-type amphoteric surfactants; nonionic surfactants such as polyoxyethylene lauryl ether, polyoxyethylene alkyl ether, polyoxyethylene alkyl phenyl ether and lauryl alcohol alkoxylate; and anionic surfactants such as sodium polyoxyethylene-alkyl phenyl ether sulfate. Each of these may be used alone, or two or more types of these may be used in combination.

More specifically, examples of the surfactant that specifically reacts with HDL3 include nonionic surfactants such as polyoxyethylene distyrene-modified phenyl ether Emulgen A90 (Kao Corporation), polyoxyethylene lauryl ether Emulgen 120 (Kao Corporation) p-isooctyl polyoxyethylene phenol formaldehyde polymer Triton-WR-1339 (Nacalai Tesque) and polyoxyethylene lauryl ether Persoft NK-100 (NOF Corporation); amphoteric surfactants such as lauryl dimethyl-aminoacetic acid betaine Nissan Anon BL-SF (NOF Corporation); and anionic surfactants such as fatty acid series phosphoric acid ester ADEKA COL PS-440E (ADEKA Corporation).

Examples of the surfactant that specifically reacts with HDL, which may be used, include nonionic surfactants having an HLB of 11 to 14 such as polyoxyethylene distyrene-modified phenyl ether, polyoxyethylene tribenzyl phenyl ether, polyoxyalkylene alkyl ether, polyoxyethylene polycyclic phenyl ether and polyoxyethylene cumyl phenyl ether; and imidazoline-type amphoteric surfactants. Specific examples of the surfactant that specifically reacts with HDL, which may be used, include Emulgen A60 (Kao Corporation), Emulgen B66 (Kao Corporation), Emulgen LS110 (Kao Corporation), Newcol-CMP-11 (Nippon Nyukazai Co, Ltd.), Newcol-710 (Nippon Nyukazai Co, Ltd.), Newcol-610 (Nippon Nyukazai Co, Ltd.), Newcol-2609 (Nippon Nyukazai Co, Ltd.) and Nissan Anon GLM-R-LV (NOF Corporation).

Examples of the surfactant that specifically reacts with all lipoproteins, which may be used, include nonionic surfactants such as polyoxyethylene lauryl ether, polyoxyethylene alkyl ether, polyoxyethylene alkyl phenyl ether and lauryl alcohol alkoxylate. Anionic surfactants such as sodium polyoxyethylene-alkyl phenyl ether sulfate may also be used. Specific examples of the surfactant that specifically reacts with all lipoproteins, which may be used, include Emulgen 707 (Kao Corporation), Emulgen 909 (Kao Corporation), Emulgen 108 (Kao Corporation), Nymeen L207 (NOF Corporation), Adekatol LB83 (ADEKA Corporation), Adekatol LB103 (ADEKA Corporation) and Newcol-707 (Nippon Nyukazai Co, Ltd.).

In Step 2, the concentration of the surfactant is preferably 0.01 to 5.0% (w/v), more preferably 0.05 to 2.0% (w/v).

In Step 2, cholesterol is quantified by the reaction of such surfactants. It should be noted that the surfactant used is different between Step 1 and Step 2. Methods of quantification per se of cholesterol are well known, and any of the well known methods may be used. A concrete description is also given in Examples below. For example, ester-type cholesterol in lipoprotein is hydrolyzed with cholesterol esterase to produce free cholesterol and a fatty acid, and the produced free cholesterol and free cholesterol inherently existing in lipoprotein are converted using cholesterol oxidase to generate cholestenone and hydrogen peroxide. A quinone pigment is then formed in the presence of peroxidase, and quantified. Examples of compounds that generate a quinone pigment include HDAOS (N-(2-hydroxy-3-sulfopropyl)-3,5-dimethoxyaniline), DAOS (N-ethyl-N(-2-hydroxy-3-sulfopropyl)-3,5-dimethoxyaniline sodium salt) or TOOS (N-ethyl-N(-2-hydroxy-3-sulfopropyl)-3-methylaniline sodium salt dihydrate) and 4-aminoantipyrine, but the compounds are not restricted as long as the combination allows generation of a quinone pigment. In cases where cholesterol esterase and cholesterol oxidase are used in Step 1, the cholesterol esterase and cholesterol oxidase used in Step 1 may be used as they are in Step 2 without further addition.

The concentration of the compound for generation of a quinone pigment is preferably about 0.5 to about 2.0 mmol/L in the case of HDAOS, or 0.1 to 2.0 mmol/L in the case of 4-aminoantipyrine. The concentration of peroxidase is preferably 0.4 to 5.0 U/mL. In a process wherein hydrogen peroxide produced in Step 1 is decomposed using catalase, a catalase inhibitor sodium azide is used by addition to the reaction liquid in Step 2. The concentration of sodium azide in this case is usually about 0.1 g/L to about 1.0 g/L.

The other reaction conditions for Step 2 (reaction temperature, time, buffer, pH and the like) may be the same as the reaction conditions for Step 1 described above.

Further, it is also possible to calculate the HDL2 cholesterol level in the test sample by subtracting the HDL3 cholesterol level obtained by Step 1 and Step 2 from the HDL cholesterol level in the test sample. Since methods for determining the HDL cholesterol level in a test sample are well known (e.g., JP 2001-103998 A) and kits for such methods are commercially available, the quantification can be easily carried out using these.

The present invention will now be described more concretely by way of Examples below. However, the present invention is not limited to the Examples below.

EXAMPLES

Reference Example 1

Reagent A and Reagent B having the compositions described below were prepared, and reagents were prepared by adding various surfactants to Reagent A to a concentration of 0.1% (w/v) or 1.0% (w/v). Immediately before the measurement, Reagent A containing the various surfactants described below was mixed with Reagent B at a ratio of 1:3. Cholesterol in each of the HDL2 fraction and the HDL3 fraction was reacted with the resulting mixture, and the final absorbances at a main wavelength of 700 nm and a sub-wavelength of 600 nm were measured and compared.

Fractionation was carried out to obtain the HDL2 fraction and the HDL3 fraction as follows. A test sample containing HDL, that is, serum was subjected to ultracentrifugation using a solution with sodium chloride and sodium bromide such that separation occurs at a density at the border between HDL2 and HDL3 (1.125), and each resulting fraction was recovered.

Table 1 below shows surfactants with which the ratio of HDL2/HDL3 was not more than 0.75 and the ratios of CM-IDL/HDL3 and LDL/HDL3 were not more than 0.75. These surfactants were determined to be surfactants that react with HDL3. Table 2 shows surfactants with which the ratio of HDL2/HDL3 was not less than 1.25 and the ratios of CM-IDL/HDL2 and LDL/HDL2 were not less than 1.25. These surfactants were determined to be surfactants that react with lipoproteins other than HDL3. Table 3 shows surfactants with which the ratio of HDL2/HDL3 was between 0.75 and 1.25 and the ratios of CM-IDL/HDL2, LDL/HDL2, CM-IDL/HDL3 and LDL/HDL3 were not more than 0.75. These surfactants were determined to be surfactants that react with HDL. Table 4 shows surfactants with which the ratio of HDL2/HDL3 was between 0.75 and 1.25 and the ratios of CM-IDL/HDL2, LDL/HDL2, CM-IDL/HDL3 and LDL/HDL3 were not less than 0.75. These surfactants were determined to be surfactants that react with all lipoproteins. Table 5 shows surfactants that could not be grouped into any of the above categories. These surfactants were determined to be surfactants that react with lipoproteins other than HDL.

Reagent A

| | |
|---|---|
| BES buffer (pH 7.0) | 100 mmol/L |
| HDAOS | 0.7 mmol/L |
| Catalase | 600 U/L |
| Cholesterol oxidase | 1.4 U/mL |
| Cholesterol esterase | 0.8 U/mL |

Reagent B

| | |
|---|---|
| BES buffer (pH 6.6) | 100 mmol/L |
| Sodium azide | 0.1 % |
| 4-Aminoantipyrine | 4.0 mmol/L |
| Peroxidase | 2.4 U/mL |

TABLE 1

| | Concentration | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen A90 | 1% | 219 | 161 | 339 | 448 | 0.76 | 0.65 | 0.49 | 0.47 | 0.36 |
| | 0.1% | 198 | 119 | 306 | 519 | 0.59 | 0.65 | 0.38 | 0.39 | 0.23 |
| Emulgen 120 | 1% | 560 | 564 | 806 | 1267 | 0.64 | 0.69 | 0.44 | 0.70 | 0.45 |
| | 0.1% | 494 | 465 | 499 | 793 | 0.63 | 0.99 | 0.62 | 0.93 | 0.59 |
| Nissan Anon | 1% | 441 | 941 | 721 | 1244 | 0.58 | 0.61 | 0.35 | 1.31 | 0.76 |
| BL-SF | 0.1% | 396 | 290 | 321 | 294 | 1.09 | 1.23 | 1.35 | 0.90 | 0.99 |
| Triton WR- | 1% | 317 | 216 | 560 | 972 | 0.58 | 0.57 | 0.33 | 0.39 | 0.22 |
| 1339 | 0.1% | 203 | 117 | 385 | 582 | 0.66 | 0.53 | 0.35 | 0.30 | 0.20 |
| Persoft NK- | 1% | 687 | 603 | 1036 | 1569 | 0.66 | 0.66 | 0.44 | 0.58 | 0.38 |
| 100 | 0.1% | 503 | 421 | 648 | 785 | 0.83 | 0.78 | 0.64 | 0.65 | 0.54 |
| Adekatol PS- | 1% | 771 | 1099 | 1124 | 1633 | 0.69 | 0.69 | 0.47 | 0.98 | 0.67 |
| 440E | 0.1% | 1019 | 1410 | 1555 | 1715 | 0.91 | 0.66 | 0.59 | 0.91 | 0.82 |

(Unit: Abs × 10000)

Emulgen A90, Emulgen 120, Nissan Anon BL-SF, Triton WR-1339, Persoft NK-100 and Adekatol PS-440E were surfactants that specifically react with HDL3.

TABLE 2

| | Concentration | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen A500 | 1% | 27 | 77 | 105 | 86 | 1.22 | 0.26 | 0.31 | 0.73 | 0.90 |
| | 0.1% | 105 | 44 | 36 | 20 | 1.80 | 2.92 | 5.25 | 1.22 | 2.20 |
| Nissan Anon BDF-SF | 1% | 304 | 226 | 328 | 242 | 1.36 | 0.93 | 1.26 | 0.69 | 0.93 |
| | 0.1% | 272 | 91 | 82 | 42 | 1.95 | 3.32 | 6.48 | 1.11 | 2.17 |
| Nissan Anon BF | 1% | 512 | 461 | 581 | 571 | 1.02 | 0.88 | 0.90 | 0.79 | 0.81 |
| | 0.1% | 687 | 127 | 394 | 280 | 1.41 | 1.74 | 2.45 | 0.32 | 0.45 |
| Nymeen S210 | 1% | 485 | 252 | 290 | 222 | 1.31 | 1.67 | 2.18 | 0.87 | 1.14 |
| | 0.1% | 514 | 278 | 271 | 199 | 1.36 | 1.90 | 2.58 | 1.03 | 1.40 |
| Pluronic P103 | 1% | 87 | 72 | 102 | 81 | 1.26 | 0.85 | 1.07 | 0.71 | 0.89 |
| | 0.1% | 63 | 46 | 36 | 25 | 1.44 | 1.75 | 2.52 | 1.28 | 1.84 |
| Kohtamin 24P | 1% | 495 | 185 | 359 | 288 | 1.25 | 1.38 | 1.72 | 0.52 | 0.64 |
| | 0.1% | 580 | 323 | 307 | 177 | 1.73 | 1.89 | 3.28 | 1.05 | 1.82 |
| Sunamide CF-10 | 1% | 427 | 322 | 339 | 251 | 1.35 | 1.26 | 1.70 | 0.95 | 1.28 |
| | 0.1% | 479 | 321 | 308 | 184 | 1.67 | 1.56 | 2.60 | 1.04 | 1.74 |
| Amphitol 24B | 1% | 471 | 392 | 509 | 481 | 1.06 | 0.93 | 0.98 | 0.77 | 0.81 |
| | 0.1% | 596 | 558 | 384 | 283 | 1.36 | 1.55 | 2.11 | 1.45 | 1.97 |
| Pluronic F68 | 1% | 127 | 47 | 45 | 62 | 0.73 | 2.82 | 2.05 | 1.04 | 0.76 |
| | 0.1% | 1328 | 275 | 175 | 129 | 1.36 | 7.59 | 10.29 | 1.57 | 2.13 |
| Pluronic F127 | 1% | 523 | 260 | 138 | 109 | 1.27 | 3.79 | 4.80 | 1.88 | 2.39 |
| | 0.1% | 137 | 78 | 59 | 60 | 0.98 | 2.32 | 2.28 | 1.32 | 1.30 |

(Unit: Abs × 10000)

Emulgen A500, Nissan Anon BDF-SF, Nissan Anon BF, Nymeen S210, Pluronic P103, Kohtamin 24P, Sunamide CF-10, Amphitol 24B, Pluronic F68 and Pluronic F127 were surfactants that specifically react with lipoproteins other than HDL3.

TABLE 3

| | | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen B66 | 1% | 375 | 281 | 1434 | 1473 | 0.97 | 0.26 | 0.25 | 0.20 | 0.19 |
| | 0.1% | 361 | 185 | 1396 | 1441 | 0.97 | 0.26 | 0.25 | 0.13 | 0.13 |
| Emulgen A60 | 1% | 375 | 281 | 1434 | 1473 | 0.97 | 0.26 | 0.25 | 0.20 | 0.19 |
| | 0.1% | 361 | 185 | 1396 | 1441 | 0.97 | 0.26 | 0.25 | 0.13 | 0.13 |
| Emulgen LS110 | 1% | 851 | 1267 | 1454 | 1463 | 0.99 | 0.59 | 0.58 | 0.87 | 0.87 |
| | 0.1% | 744 | 1034 | 1518 | 1529 | 0.99 | 0.49 | 0.49 | 0.68 | 0.68 |
| Newcol-610 | 1% | 500 | 447 | 1386 | 1470 | 0.94 | 0.36 | 0.34 | 0.32 | 0.30 |
| | 0.1% | 439 | 320 | 1431 | 1472 | 0.97 | 0.31 | 0.30 | 0.22 | 0.22 |
| Newcol-2609 | 1% | 636 | 553 | 1509 | 1556 | 0.97 | 0.42 | 0.41 | 0.37 | 0.36 |
| | 0.1% | 547 | 543 | 1512 | 1502 | 1.01 | 0.36 | 0.36 | 0.36 | 0.36 |
| Newcol-CMP-11 | 1% | 681 | 519 | 1498 | 1551 | 0.97 | 0.45 | 0.44 | 0.35 | 0.33 |
| | 0.1% | 542 | 371 | 1435 | 1529 | 0.94 | 0.38 | 0.35 | 0.26 | 0.24 |
| Nissan Anon GLM-R-LV | 1% | 593 | 841 | 1219 | 1214 | 1.00 | 0.49 | 0.49 | 0.69 | 0.69 |
| | 0.1% | 92 | 112 | 68 | 59 | 1.15 | 1.35 | 1.56 | 1.65 | 1.90 |
| Newcol-710 | 1% | 506 | 491 | 1303 | 1597 | 0.82 | 0.39 | 0.32 | 0.38 | 0.31 |
| | 0.1% | 400 | 297 | 1344 | 1476 | 0.91 | 0.30 | 0.27 | 0.22 | 0.20 |

(Unit: Abs × 10000)

Emulgen B66, Emulgen A60, Emulgen LS110, Newcol 610, Newcol 2609, Newcol-CMP-11, Nissan Anon GLM-RLV and Newcol-710 were surfactants that specifically react with HDL.

TABLE 4

| | | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Emulgen 108 | 1% | 2284 | 2390 | 2197 | 2202 | 1.00 | 1.04 | 1.04 | 1.09 | 1.09 |
| | 0.1% | 1609 | 1815 | 1585 | 1548 | 1.02 | 1.02 | 1.04 | 1.15 | 1.17 |
| Emulgen 707 | 1% | 3169 | 3021 | 2928 | 3048 | 0.96 | 1.08 | 1.04 | 1.03 | 0.99 |
| | 0.1% | 1186 | 1546 | 1443 | 1375 | 1.05 | 0.82 | 0.86 | 1.07 | 1.12 |
| Newcol-707 | 1% | 2349 | 2700 | 2783 | 2703 | 1.03 | 0.84 | 0.87 | 0.97 | 1.00 |
| | 0.1% | 4106 | 4766 | 4850 | 4910 | 0.99 | 0.85 | 0.84 | 0.98 | 0.97 |

TABLE 4-continued

|  |  | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Adekatol LB83 | 1% | 1592 | 1611 | 1523 | 1509 | 1.01 | 1.05 | 1.06 | 1.06 | 1.07 |
|  | 0.1% | 1661 | 1680 | 1611 | 1598 | 1.01 | 1.03 | 1.04 | 1.04 | 1.05 |
| Adekatol LB103 | 1% | 1418 | 1556 | 1533 | 1492 | 1.03 | 0.92 | 0.95 | 1.02 | 1.04 |
|  | 0.1% | 1228 | 1579 | 1582 | 1540 | 1.03 | 0.78 | 0.80 | 1.00 | 1.03 |
| Emulgen 909 | 1% | 4248 | 3432 | 3488 | 3407 | 1.02 | 1.22 | 1.25 | 0.98 | 1.01 |
|  | 0.1% | 2467 | 2607 | 2704 | 2633 | 1.03 | 0.91 | 0.94 | 0.96 | 0.99 |

(Unit: Abs × 10000)

Emulgen 108, Emulgen 707, Newcol 707, Adekatol LB83, Adekatol LB103 and Emulgen 909 were surfactants that specifically react with all lipoproteins.

TABLE 5

|  |  | CM-IDL | LDL | HDL2 | HDL3 | HDL2/HDL3 | CM-IDL/HDL2 | CM-IDL/HDL3 | LDL/HDL2 | LDL/HDL3 |
|---|---|---|---|---|---|---|---|---|---|---|
| Newcol-714 | 1% | 178 | 139 | 260 | 218 | 1.19 | 0.68 | 0.82 | 0.53 | 0.64 |
|  | 0.1% | 203 | 116 | 220 | 203 | 1.08 | 0.92 | 1.00 | 0.53 | 0.57 |
| Newcol-723 | 1% | 127 | 96 | 178 | 135 | 1.32 | 0.71 | 0.94 | 0.54 | 0.71 |
|  | 0.1% | 28 | 64 | 78 | 63 | 1.24 | 0.36 | 0.44 | 0.82 | 1.02 |
| Newcol-2614 | 1% | 137 | 111 | 211 | 177 | 1.19 | 0.65 | 0.77 | 0.53 | 0.63 |
|  | 0.1% | 142 | 84 | 143 | 103 | 1.39 | 0.99 | 1.38 | 0.59 | 0.82 |
| Nymeen S215 | 1% | 207 | 169 | 226 | 170 | 1.33 | 0.92 | 1.22 | 0.75 | 0.99 |
|  | 0.1% | 183 | 166 | 213 | 165 | 1.29 | 0.86 | 1.11 | 0.78 | 1.01 |
| Pluronic P123 | 1% | 187 | 142 | 222 | 169 | 1.31 | 0.84 | 1.11 | 0.64 | 0.84 |
|  | 0.1% | 79 | 68 | 108 | 97 | 1.11 | 0.73 | 0.81 | 0.63 | 0.70 |
| Levenol WX | 1% | 122 | 120 | 163 | 134 | 1.22 | 0.75 | 0.91 | 0.74 | 0.90 |
|  | 0.1% | 80 | 75 | 67 | 27 | 2.48 | 1.19 | 2.96 | 1.12 | 2.78 |
| Nymid MT-215 | 1% | 31 | 250 | 272 | 203 | 1.34 | 0.11 | 0.15 | 0.92 | 1.23 |
|  | 0.1% | 27 | 228 | 263 | 195 | 1.35 | 0.10 | 0.14 | 0.87 | 1.17 |
| Nonion HS220 | 1% | 329 | 268 | 322 | 253 | 1.27 | 1.02 | 1.30 | 0.83 | 1.06 |
|  | 0.1% | 223 | 182 | 280 | 224 | 1.25 | 0.80 | 1.00 | 0.65 | 0.81 |
| Pluronic F88 | 1% | 54 | 45 | 33 | 46 | 0.72 | 1.64 | 1.17 | 1.36 | 0.98 |
|  | 0.1% | 45 | 51 | 31 | 49 | 0.63 | 1.45 | 0.92 | 1.65 | 1.04 |

(Unit: Abs × 10000)

Newcol-714, Newcol-723, Newcol-2614, Nymeen 5215, Pluronic P123, Levenol WX, Nymid MT-215, Nonion HS220 and Pluronic F88 were surfactants that specifically react with lipoproteins other than HDL.

Example 1

Reagent C for elimination of cholesterol other than HDL3, and Reagent D for the step of measuring HDL in the product obtained by reaction with Reagent C were prepared according to the compositions below. Sixteen samples of serum were subjected to the measurement, and the results were analyzed in teams of correlation with results by the HDL3 precipitation method. As a control for the prepared reagents, HDL Measurement Reagent (manufactured by Denka Seiken Co., Ltd.) was used.

In the measurement, 150 μL of Reagent C described below was added to 2 μL of serum, and the reaction was allowed to proceed for 5 minutes with warming, followed by addition of Reagent D to the reaction solution and additional 5 minutes of reaction with warming. The absorbances at a main wavelength of 700 nm and a sub-wavelength of 600 nm were measured. The operation of the known HDL3 precipitation method was performed according to JP 2009-207463 A. The serum was subjected to measurement with HDL Measurement Reagent, and the results were similarly analyzed in terms of correlation with the results by the HDL3 precipitation method (hereinafter referred to as Measurement Method A) for comparison with the prepared reagents.

Reagent C

| BES buffer (pH 7.0) | 100 mmol/L |
|---|---|
| HDAOS | 0.7 mmol/L |
| Sunamide CF-10 | 1% |
| Catalase | 600 U/L |
| Cholesterol oxidase | 1.4 U/mL |
| Cholesterol esterase | 0.8 U/mL |

Reagent D

| BES buffer (pH 6.6) | 100 mmol/L |
|---|---|
| Sodium azide | 0.1% |
| Emulgen B66 | 1.5% |
| 4-Aminoantipyrine | 4.0 mmol/L |
| Peroxidase | 2.4 U/mL |

Figure 1:
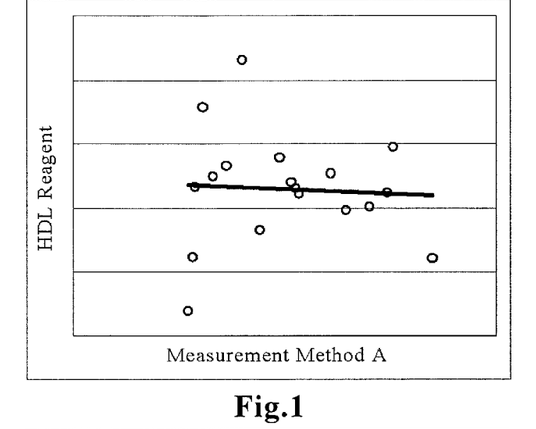
FIG. 1 shows a correlation diagram between measurement results obtained by a known HDL precipitation method (Measurement Method A) and measurement results obtained using a commercially available HDL measurement reagent.
Figure 2:
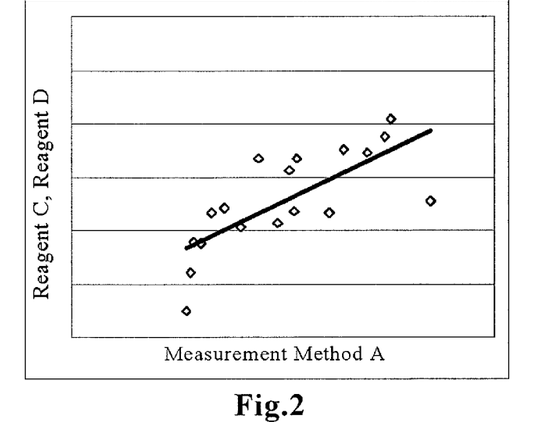
FIG. 2 shows a correlation diagram between measurement results obtained by a known HDL precipitation method (Measurement Method A) and measurement results obtained by the quantification method of the present invention.

Correlation diagrams are shown in FIG. 1 and FIG. 2. FIG. 1 shows a correlation diagram between Measurement Method A and HDL Measurement Reagent, and FIG. 2 shows a correlation diagram between Measurement Method A, and Reagent C and Reagent D.

The correlation coefficient between HDL and the HDL3 precipitation method was: $r=-0.051$, and the measured value for Reagents C and D had a correlation coefficient of: $r=0.74$ with the HDL3 precipitation method. Thus, compared to the HDL measurement method, measurement using Reagents C and D had a better correlation with HDL3, and more specific measurement of HDL3 was possible.

Figure 3:
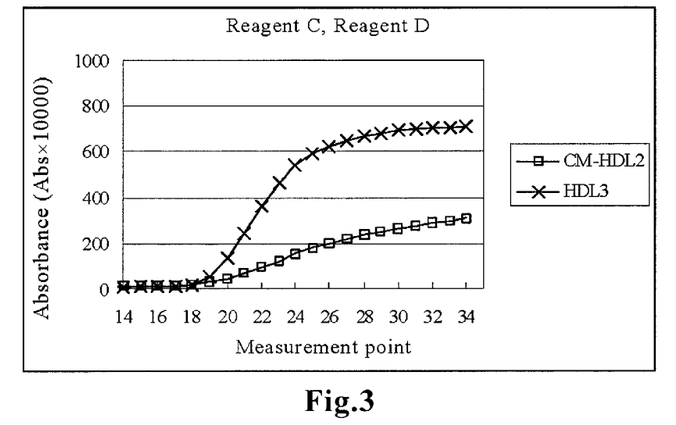
FIG. 3 shows a diagram illustrating a result of Examples of the present invention in terms of changes in the absorbance of each fraction after addition of Reagent D in Step 2.

Further, fractionation by ultracentrifugation was carried out to obtain the CM-HDL2 fraction and the HDL3 fraction, and each fraction was subjected to measurement with the above-described reagents, wherein the absorbance was measured at each measurement time. The result in terms of changes in the absorbance after addition of Reagent D is shown in FIG. 3. As is evident from FIG. 3, the reaction occurred more specifically to HDL3 than to lipoproteins other than HDL3.

Example 2

Fractionation by ultracentrifugation was carried out to obtain the CM-LDL fraction, HDL2 fraction and HDL3 fraction, and each fraction was reacted with Reagent E prepared by adding phospholipase D (PLDP) to Reagent A used in Reference Example 1. Reagent D described above was further added to the reaction solution to perform measurement. In the measurement, 150 μL of Reagent E was added to 2 μL of serum, and the reaction was allowed to proceed for 5 minutes with warming, followed by addition of Reagent D to the reaction solution and additional 5 minutes of reaction with warming. The absorbances at a main wavelength of 700 nm and a sub-wavelength of 600 nm were measured.

Reagent E

| BES buffer (pH 7.0) | 100 mmol/L |
|---|---|
| HDAOS | 0.7 mmol/L |
| Catalase | 600 U/L |
| Cholesterol oxidase | 1.4 U/mL |
| Cholesterol esterase | 0.8 U/mL |
| Phospholipase D | 5.0 U/mL |

Figure 4:
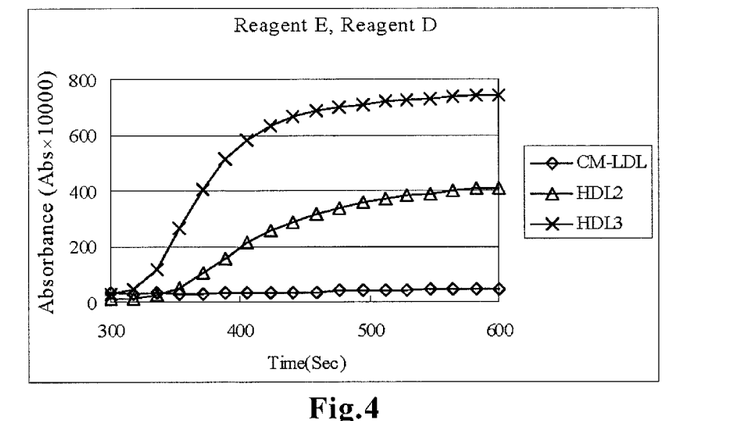
FIG. 4 shows a diagram illustrating a result of Examples of the present invention in terms of changes in the absorbance of each fraction after addition of Reagent D in Step 2.

FIG. 4 shows the result in terms of changes in the absorbance with time of each fraction after addition of Reagent D. Specific reaction with HDL3 can be seen.

Example 3

Reagent F was prepared by adding a surfactant and sphingomyelinase to Reagent A used in Reference Example 1, and Reagent G was prepared for the step of measuring HDL3 in the product obtained by reaction with Reagent F. The compositions of these reagents were as shown below. Fractionation was carried out by ultracentrifugation to obtain the fraction from CM to IDL, LDL fraction, HDL2 fraction and HDL3 fraction, and the obtained fractions were subjected to measurement. The procedure for measurement with the reagents was the same as in Example 2. The absorbance was measured at each measurement time.

Reagent F

| BES buffer (pH 7.0) | 100 mmol/L |
|---|---|
| HDAOS | 0.7 mmol/L |
| Pluronic F68 | 0.03 w/v % |
| Catalase | 600 U/L |
| Cholesterol oxidase | 1.4 U/mL |
| Cholesterol esterase | 0.8 U/mL |
| Sphingomyelinase | 0.5 U/mL |

Reagent G

| BES buffer (pH 6.6) | 100 mmol/L |
|---|---|
| Sodium azide | 0.1% |
| Emulgen A90 | 2.0% |
| 4-Aminoantipyrine | 4.0 mmol/L |
| Peroxidase | 2.4 U/mL |

Figure 5:
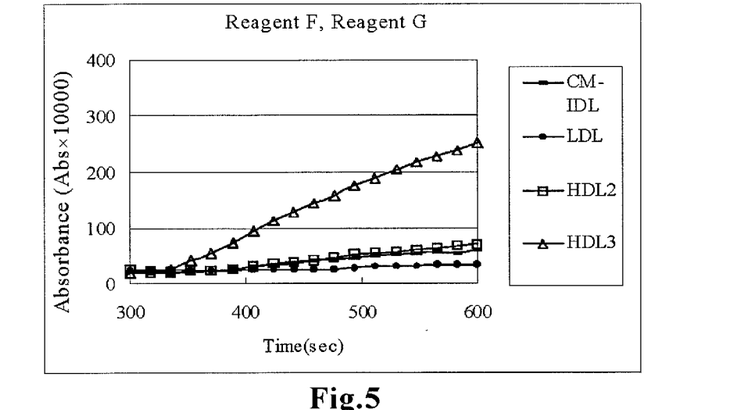
FIG. 5 shows a diagram illustrating a result of Examples of the present invention in terms of changes in the absorbance of each fraction after addition of Reagent G in Step 2.

FIG. 5 shows the result in terms of changes in the absorbance with time of each fraction after addition of Reagent G. Specific reaction with HDL3 can be seen.

Example 4

The absorbance was measured in the same manner as in Example 3 using Reagent H which was prepared with the same composition as that of Reagent E used in Example 2 except that phospholipase C was used as the phospholipase and a surfactant was added.

Reagent H

| BES buffer (pH 7.0) | 100 mmol/L |
|---|---|
| HDAOS | 0.7 mmol/L |
| Pluronic F68 | 0.03 w/v % |
| Catalase | 600 U/L |
| Cholesterol oxidase | 1.4 U/mL |
| Cholesterol esterase | 0.8 U/mL |
| Phospholipase C | 5.0 U/mL |

Figure 6:
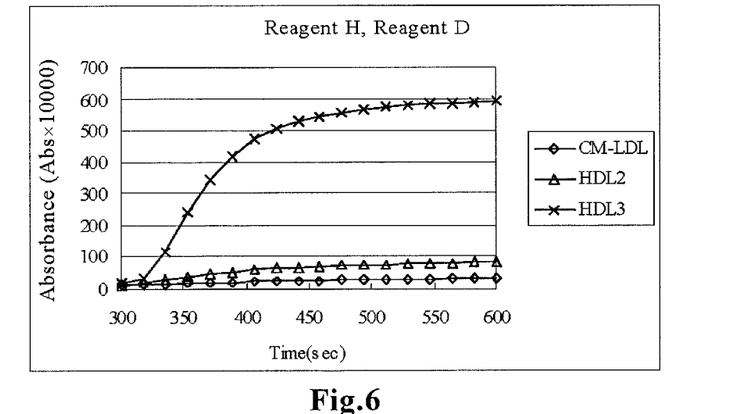
FIG. 6 shows a diagram illustrating a result of Examples of the present invention in terms of changes in the absorbance of each fraction after addition of Reagent H in Step 2.

FIG. 6 shows the result in terms of changes in the absorbance with time of each fraction after addition of Reagent H. Specific reaction with HDL3 can be seen.

Example 5

The absorbance was measured in the same manner as in Example 3 using Reagent I which was prepared with the same composition as that of Reagent H used in Example 4 except that phospholipase D (PLDP) was used as the phospholipase and a surfactant was added.

Reagent I

| BES buffer (pH 7.0) | 100 mmol/L |
|---|---|
| HDAOS | 0.7 mmol/L |
| Pluronic F68 | 0.03 w/v % |
| Catalase | 600 U/L |
| Cholesterol oxidase | 1.4 U/mL |
| Cholesterol esterase | 0.8 U/mL |
| Phospholipase D | 5.0 U/mL |

Figure 7:
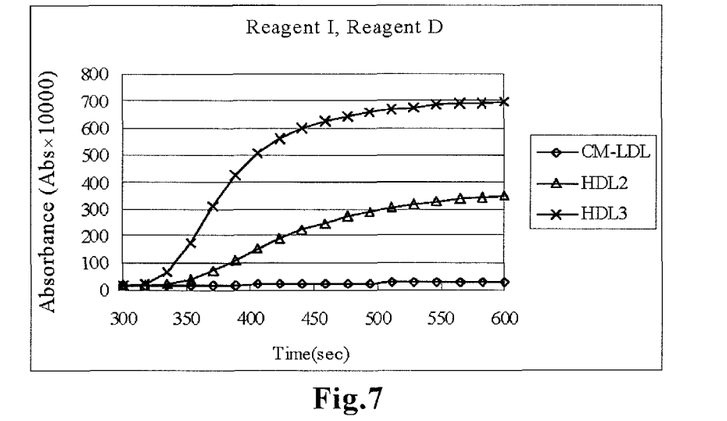
FIG. 7 shows a diagram illustrating a result of Examples of the present invention in terms of changes in the absorbance of each fraction after addition of Reagent I in Step 2.

FIG. 7 shows the result in terms of changes in the absorbance with time of each fraction after addition of Reagent I. Specific reaction with HDL3 can be seen.

Example 6

The absorbance was measured in the same manner as in Example 3 except that Reagent J and Reagent K having the compositions described below were used.

Reagent J

| BES buffer (pH 7.0) | 100 mmol/L |
|---|---|
| HDAOS | 0.7 mmol/L |
| Pluronic P103 | 0.03 w/v % |
| Catalase | 600 U/L |
| Cholesterol oxidase | 1.4 U/mL |
| Cholesterol esterase | 0.8 U/mL |
| Phospholipase D | 5.0 U/mL |

Reagent K

| BES buffer (pH 6.6) | 100 mmol/L |
|---|---|
| Sodium azide | 0.1% |
| Emulgen 120 | 1.0% |
| 4-Aminoantipyrine | 4.0 mmol/L |
| Peroxidase | 2.4 U/mL |

Figure 8:
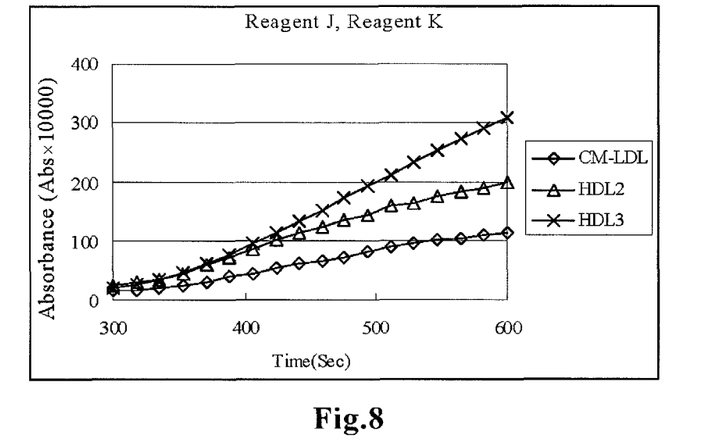
FIG. 8 shows a diagram illustrating a result of Examples of the present invention in terms of changes in the absorbance of each fraction after addition of Reagent K in Step 2.

FIG. 8 shows the result in terms of changes in the absorbance with time of each fraction after addition of Reagent K. Specific reaction with HDL3 can be seen.

Example 7

The absorbance was measured in the same manner as in Example 3 except that Reagent J used in Example 5 and Reagent L having the composition described below were used.

Reagent L

| BES buffer (pH 6.6) | 100 mmol/L |
|---|---|
| Sodium azide | 0.1% |
| Emulgen 909 | 1.0% |
| 4-Aminoantipyrine | 4.0 mmol/L |
| Peroxidase | 2.4 U/mL |

Figure 9:
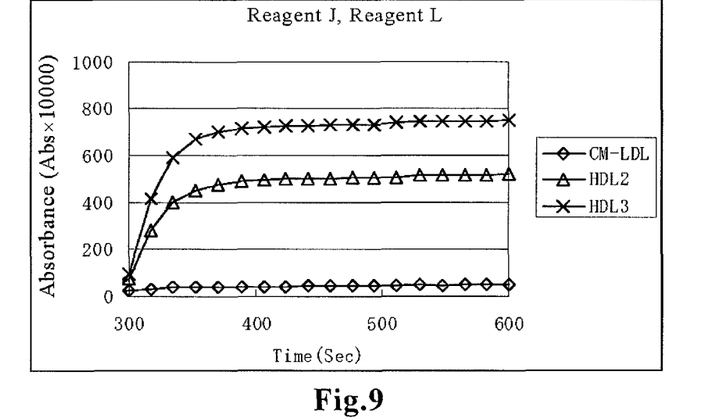
FIG. 9 shows a diagram illustrating a result of Examples of the present invention in terms of changes in the absorbance of each fraction after addition of Reagent L in Step 2.

FIG. 9 shows the result in terms of changes in the absorbance with time of each fraction after addition of Reagent L. Specific reaction with HDL3 can be seen.

Example 8

Reagent M was prepared and used in combination with Reagent D to measure HDL-C (C represents cholesterol; the same applies hereinafter) in the test sample. From this value, the value obtained by measuring HDL3-C using Reagent I and Reagent D in Example 5 was subtracted, to calculate HDL2-C. The values of HDL-C, HDL3-C and HDL2-C in each sample were as shown in Table 6.

Reagent M

| BES buffer (pH 7.0) | 100 mmol/L |
|---|---|
| HDAOS | 0.7 mmol/L |
| Pluronic P88 | 0.1 w/v % |
| Catalase | 600 U/L |
| Cholesterol oxidase | 1.4 U/mL |
| Cholesterol esterase | 0.8 U/mL |
| Phospholipase D | 5.0 U/mL |

TABLE 6

| HDL-C | HDL3-C | HDL2-C |
|---|---|---|
| 84.5 | 50.0 | 34.5 |
| 85.1 | 49.9 | 35.2 |
| 99.0 | 57.1 | 41.9 |
| 88.2 | 45.2 | 43.0 |
| 86.6 | 49.9 | 36.7 |

(Unit: mAbs)

The invention claimed is:

1. A method for quantifying cholesterol in high-density lipoprotein 3 (HDL3), said method comprising:
   Step 1 reacting with a test sample in a reaction system, a surfactant(s) that react(s) with substantially all lipoproteins other than HDL3 to transfer cholesterol of the lipoproteins other than HDL3 to the outside of the reaction system; and
   Step 2 wherein cholesterol remaining in the reaction system is quantified.

2. The method according to claim 1, wherein said surfactant is at least one nonionic surfactant which is polyoxyethylene distyrene-modified phenyl ether.

3. The method according to claim 1, wherein said surfactant is at least one nonionic surfactant selected from the group consisting of polyoxyethylene-polyoxypropylene condensates and polyoxyethylene-stearylamine, and/or anionic surfactant amide ether sulfate.

4. The method according to claim 1, wherein said surfactant is at least one amphoteric surfactant selected from the group consisting of coconut oil fatty acid-amidopropyldimethyl-aminoacetic acid betaine, alkyl dimethyl-aminoacetic acid betaine and lauryl betaine.

5. The method according to claim 1, wherein said surfactant is a cationic surfactant which is lauryl trimethyl ammonium chloride.

6. The method according to claim 1, wherein said Step 2 is carried out in the presence of a surfactant(s) that react(s) at least HDL3.

7. The method according to claim 6, wherein said surfactant used in Step 2 is at least one nonionic surfactant selected from the group consisting of polyoxyethylene lauryl ether and p-isooctyl polyoxyethylene phenol formaldehyde polymers.

8. The method according to claim 6, wherein said surfactant used in Step 2 is amphoteric surfactant lauryl dimethyl-aminoacetic acid betaine and/or nonionic surfactant polyoxyethylene lauryl ether.

9. The method according to claim 6, wherein said surfactant used in Step 2 is at least one anionic surfactant which is fatty acid series phosphoric acid ester.

10. The method according to claim 6, wherein said surfactant used in Step 2 is at least one nonionic surfactant having an HLB of 11 to 14, selected from the group consisting of polyoxyethylene tribenzyl phenyl ether, polyoxyalkylene alkyl ether, polyoxyethylene polycyclic phenyl ether and polyoxyethylene cumyl phenyl ether.

11. The method according to claim 6, wherein said surfactant used in Step 2 is at least one imidazoline-type amphoteric surfactant.

12. The method according to claim 6, wherein said surfactant used in Step 2 is at least one type selected from the group consisting of polyoxyethylene lauryl ether, polyoxyethylene alkyl ether and polyoxyethylene alkyl phenyl ether.

13. The method according to claim 6, wherein said surfactant used in Step 2 is nonionic surfactant lauryl alcohol alkoxylate and/or anionic surfactant sodium polyoxyethylene-alkyl phenyl ether sulfate.

* * * * *